United States Patent [19]

Heironimus et al.

[11] Patent Number: 5,607,411

[45] Date of Patent: Mar. 4, 1997

[54] CONTAINMENT AND TREATMENT ASPIRATOR SYSTEM AND METHOD

[75] Inventors: Scott N. Heironimus, 16222 Tother Rd., Leo, Ind. 46765; Peter G. El-Sabaaly, Waukesha; John B. Pludeman, Brookfield, both of Wis.

[73] Assignee: Scott N. Heironimus, Fort Wayne, Ind.

[21] Appl. No.: 833,144

[22] Filed: Feb. 10, 1992

[51] Int. Cl.[6] .............................. A61M 1/00; A01N 1/00; B67C 3/16
[52] U.S. Cl. .................. 604/319; 604/317; 604/320; 604/322; 128/760; 27/24.1; 137/205
[58] Field of Search .................... 604/317–320, 604/322, 323, 416; 27/22.1–24.1; 128/760, 768; 137/205, 209; 417/40

[56] References Cited

U.S. PATENT DOCUMENTS

| | | |
|---|---|---|
| 171,332 | 12/1875 | Whelan . |
| 488,338 | 12/1892 | Martin . |
| 755,556 | 3/1904 | Wilfong, Jr. . |
| 1,557,779 | 10/1925 | Scheib . |
| 2,118,704 | 5/1938 | Grontkowski ............... 27/24.1 |
| 2,124,121 | 7/1938 | Postlewait . |
| 2,149,777 | 3/1939 | Kidwell . |
| 2,462,617 | 2/1949 | Eckels . |
| 2,534,808 | 12/1950 | Bevington, Jr. . |
| 2,558,279 | 6/1951 | Sutherland, Jr. . |
| 2,784,717 | 3/1957 | Thompson . |
| 2,836,877 | 6/1958 | Hannahan . |
| 3,090,095 | 5/1963 | Moore . |
| 3,528,146 | 9/1970 | Markarian et al. . |
| 3,646,935 | 3/1972 | Holbrook et al. ............ 604/319 |
| 3,775,951 | 12/1973 | Eicholz et al. . |
| 3,861,393 | 1/1975 | Durand .............. 27/24.2 X |
| 3,863,634 | 2/1975 | Reynolds et al. . |
| 3,878,962 | 4/1975 | Holbrook et al. . |
| 3,908,246 | 9/1975 | Hannahan . |
| 3,938,540 | 2/1976 | Holbrook et al. . |
| 3,945,392 | 3/1976 | Deaton et al. . |
| 4,430,084 | 2/1984 | Deaton . |
| 4,441,860 | 4/1984 | Tsujimoto ............... 417/40 |
| 4,449,984 | 5/1984 | Cruz . |
| 4,784,156 | 11/1988 | Garg .................. 604/169 X |
| 4,832,044 | 5/1989 | Garg .................. 604/169 X |
| 4,840,184 | 6/1989 | Garg .................. 604/169 X |
| 4,844,087 | 7/1989 | Garg .................. 604/169 X |
| 4,963,094 | 10/1990 | Meyer ................... 604/320 |
| 4,982,481 | 1/1991 | Deutscher .............. 27/21.1 |
| 5,093,969 | 3/1992 | McGuire ............ 27/23.1 X |
| 5,114,416 | 5/1992 | Karwoski et al. ......... 604/317 |
| 5,149,325 | 9/1992 | Telang et al. ........ 604/319 X |
| 5,185,007 | 2/1993 | Middaugh et al. ....... 604/319 |
| 5,242,434 | 9/1993 | Terry ................. 604/317 |

OTHER PUBLICATIONS

The Champion Co.; Electro Aspirator; brochure.
Alloy Products Corp.; Portable Pressure Vessels; brochure.

*Primary Examiner*—John G. Weiss
*Assistant Examiner*—Dennis Ruhl
*Attorney, Agent, or Firm*—Barnes & Thornburg

[57] ABSTRACT

A hollow vessel with a top and a bottom. The top has a pair of ports therein. An inlet conduit is secured to one of the ports and terminates adjacent the bottom. The inlet conduit has a distal end adapted to be fixed with a trocar. The bottom bas a discharge opening with a valve. A vacuum/pressure source is located exterior of the hollow vessel. The vacuum/pressure source is connected to the other port by a second conduit with valving, a liquid trap, and pressure controls. The vessel may be used in accordance with the method to aspirate the veined and arterial network of a corpse during an embalming process.

25 Claims, 3 Drawing Sheets

CONTAINMENT AND TREATMENT ASPIRATOR SYSTEM AND METHOD

BACKGROUND OF THE INVENTION

The present invention pertains to aspirating devices and more particularly pertains to an aspirator for collection, containment and treatment of potentially hazardous flowable materials.

Many flowable materials, blood, body fluids and industrial waste products, for example, once believed to be harmless to human beings are now known to be extremely hazardous. Therefore, handling and treatment of these materials requires as little contact with the surrounding environment as possible. This is especially true when dealing with body fluids from persons having AIDS in the health care and undertaking industries.

An aspirating device for collecting hazardous flowable materials is composed of a hollow container with an inlet and a motorized pump for drawing the fluid into the container. It is often highly desirable to provide an appropriate amount of disinfectant, neutralizing agent, or germicide in the container for neutralization or other treatment of the aspirated fluid. Aspirators currently in use bare the fluid being mixed with water or other flushing fluid and both fluids are circulated through a pump and then into a container. This presents a problem in that coagulums may tend to build up in the pump and cause the pump to aspirate or discharge at fluctuating pressures that may cause the pump to rust and the motor driving the pump to overheat and break down. Additionally, fluctuations in pressure can cause accidental spillage endangering the health of all persons in the vicinity.

Sometimes, hazardous flowable materials or treated hazardous flowable materials have been discharged into storm sewers, rivers, and the like.

Aspirating devices for hazardous flowable materials now must be self contained for convenient and safe transport of hazardous fluid for proper disposal. This is especially true in the United States in light of the requirements of the Environmental Protection Agency of the United States Government. In the past, aspirator devices have failed to provide a safe device for aspirating potentially hazardous flowable materials, including body and arterial fluid, and treating and discharging the same in accordance with EPA requirements without exposure to human beings.

It is therefore highly desirable to provide an improved containment and treatment aspirator system.

It is also highly desirable to provide an improved containment and treatment aspirator system which can be utilized in an improved aspirating method which can be used to embalm a corpse.

It is also highly desirable to provide an improved containment and treatment aspirator system whereby the potentially hazardous flowable material does not circulate through the pump.

It is also highly desirable to provide an improved containment and treatment aspirator system which can provide a relatively constant vacuum and discharge pressures.

It is also highly desirable to provide an improved containment and treatment aspirator system which meets all EPA hazardous material requirements.

It is also highly desirable to provide an improved containment and treatment aspirator system that is odorless, reduced noise, self-contained and conveniently transportable.

It is also highly desirable to provide an improved containment and treatment aspirator system in which the potentially hazardous flowable material can be collected, treated, contained and disposed without exposure to human beings.

It is also highly desirable to provide an improved containment and treatment aspirator system which has a containment vessel having a volume suitable for containing the potentially hazardous flowable material of a number of aspirations before needing to be emptied and cleaned.

It is finally highly desirable to provide an improved containment and treatment aspirator system which meets all of above desired features.

SUMMARY OF THE INVENTION

It is an object of the invention to provide an improved containment and treatment aspirator system.

It is also an object of the invention to provide an improved containment and treatment aspirator system which can be utilized in an improved aspirating method which can be used to embalm a corpse.

It is also an object of the invention to provide an improved containment and treatment aspirator system whereby the potentially hazardous flowable material does not circulate through the pump.

It is also an object of the invention to provide an improved containment and treatment aspirator system which can provide a relatively constant vacuum and discharge pressures.

It is also an object of the invention to provide an improved containment and treatment aspirator system which meets all EPA hazardous material requirements.

It is also an object of the invention to provide an improved containment and treatment aspirator system that is odorless, reduced noise, self-contained and conveniently transportable.

It is also an object of the invention to provide an improved containment and treatment aspirator system in which the potentially hazardous flowable material can be collected, treated, contained and disposed without exposure to human beings.

It is also an object of the invention to provide an improved containment and treatment aspirator system which has a containment vessel having a volume suitable for containing the potentially hazardous flowable material of a number of aspirations before needing to be emptied and cleaned.

It is finally an object of the invention to provide an improved containment and treatment aspirator system which meets all of above desired features.

In the broader aspects of the invention, there is provided a hollow vessel with a top and a bottom. The top has a pair of ports therein. An inlet conduit is secured to one of the ports and terminates adjacent the bottom. The inlet conduit bas a distal end adapted to be fixed with a trocar. The bottom bas a discharge opening with a valve. A vacuum/pressure source is located exterior of the hollow vessel. The vacuum/pressure source is connected to the other port by a second conduit with valving, a liquid trap, and pressure controls. The vessel may be used in accordance with the method to aspirate the veined and arterial network of a corpse during an embalming process.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
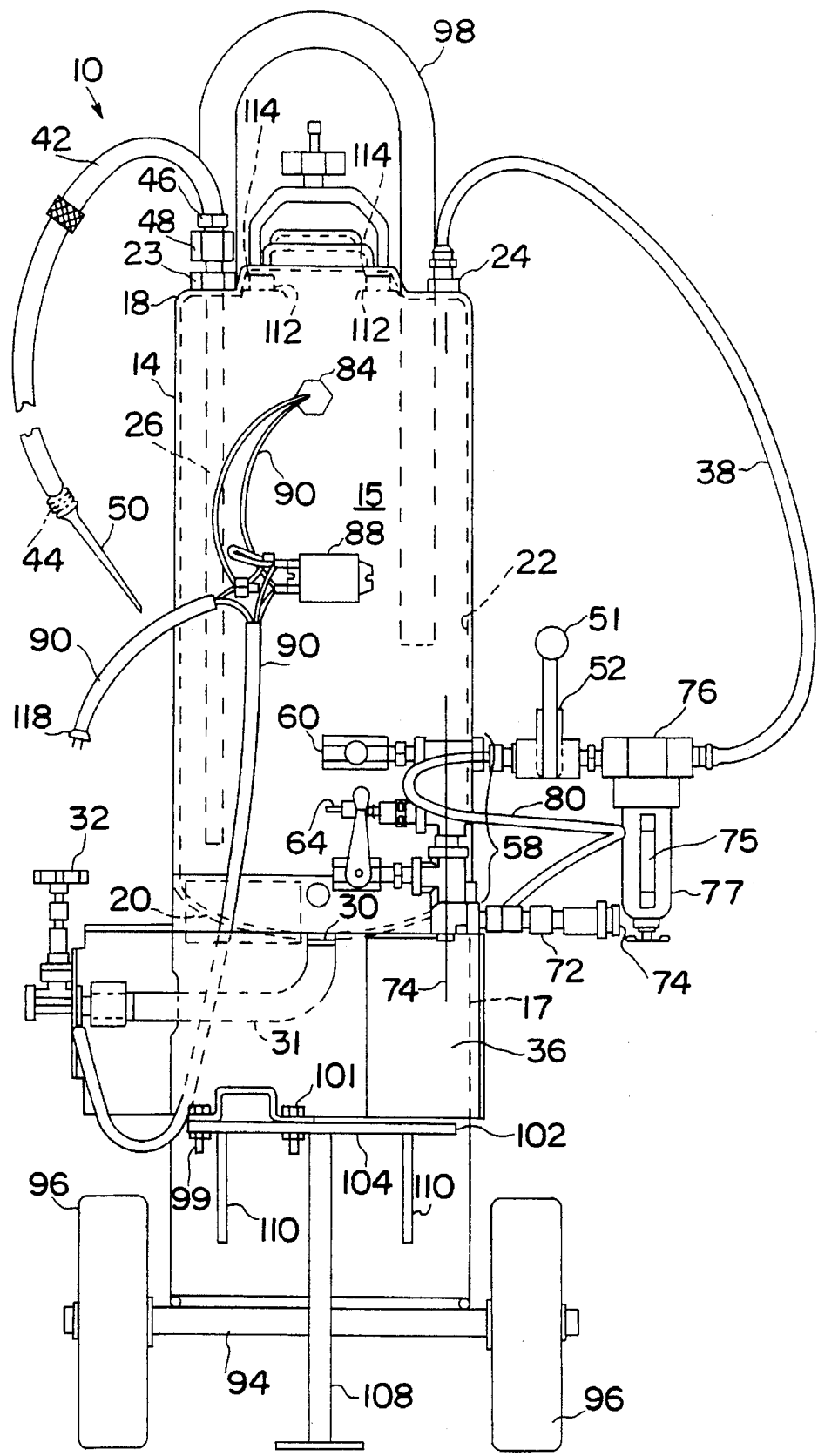
FIG. 1 is a front view of the containment and treatment aspirator system of the invention.

The containment and treatment aspirator system 10 of the invention has a hollow vessel 14 with a top 18 and a bottom 20. Vessel 14 is made of plastic or metal. In a specific embodiment for the embalming industry, vessel 14 is made of 316 stainless steel. The interior of vessel 14 is generally cylindrically shaped with rounded ends so that coagulums cannot build up inside vessel 14. Vessel 14 is supported on hollow base 17. Hollow base 17 is generally continuous with vessel 14 and extends downwardly below bottom 20 of vessel 14.

Top 18 has inlet port 23 and outlet port 24. Inlet port 23 and outlet port 24 are of a standard size so that standard fittings can attach conduits 26, 38 and 2. First conduit 26 is positioned within interior 22 and is secured to inlet port 23. First conduit 26 extends downwardly and is adjacent to but spaced from bottom 20. Outlet port 24 bas a second conduit 38 secured thereto. Second conduit 38 connects outlet port 24 to liquid trap 76. Liquid trap 76 has cup 77 and window 75. Window 75 allows for viewing the contents of cup 77. Liquid trap 76 is connected to valving 51 and 58 as will be mentioned hereinafter. Third conduit 42 is also secured to inlet port 23 and is positioned externally of vessel 14. Conduit 42 has port end 46 and distal end 44. Port end 46 is secured to inlet port 23 through valve 48. Valve 48 has both an open and a closed position and an intermediate position. Third conduit 42 may be as long as necessary for efficiently performing a particular aspiration. One embodiment of the containment and treatment aspirator system 10 of the invention used by undertakers for aspiration of body fluids in the embalming process bas a trocar 50 secured to receiving end 44.

Control valve 52 is positioned between and connects liquid trap 76 and valving 58. Control valve 52 is movable between a vacuum position 54 and a pressure discharge position 56. Control valve 52 is connected to vacuum source 36 by valving 58. Valving 58 includes vacuum regulator 60, relief valve 64 and emergency relief valve 68 positioned continuously with vacuum regulator 60 and relief valve 64 extending downwardly to emergency relief valve 68 along axis 74, as shown in FIG. 1. Control valve 52 and valving 58 are made of suitable plumbing material such as plastic or brass.

A vacuum/pressure source mount 100 is secured to base 17. Mount 100 has a platform 102 with front ledge 103 and bottom surface 104 extending from base 17. A pair of supports 110 and leg 108 are secured to bottom surface 104. Supports 110 are angularly disposed, extending between base 17 and bottom surface 104 of platform 102. Leg 108 extends downwardly from bottom surface 104 to support containment and treatment aspirator system 10 on a supporting surface.

A vacuum/pressure source 36 is mounted on platform 102 adjacent base 17 by, in the specific embodiment illustrated, bolts 101 and nuts 99.

Vacuum/pressure source 36 extends outwardly from vessel 14. In a specific embodiment, vacuum/pressure source 36 is an electric motor driven pump. In another specific embodiment, vacuum/pressure source 36 is a gasoline engine driven pump.

Referring to FIG. 1, hollow vessel 14 has float 84 within interior 22. Float 84 is electrically connected to external switch or relay 88. External switch/relay 88 is electrically connected to vacuum/pressure source 36 and power source 103 by insulated wires 90 and 118. In a specific embodiment, power source 103 is a standard 115 volt alternating power source.

Bottom 20 of hollow vessel 14 has drain opening 30 with drain conduit 31 secured thereto. Drain conduit 31 extends from bottom 20 and has gate valve 32 secured therein.

Vacuum/pressure source 36 has pressure regulator 72 secured thereto. Fourth conduit 80 connects control valve 52 to pressure regulator 72.

Base 17 has an axle 94 with a pair of wheels 96 rotatably secured at each end. Top 18 has a cleaning port 111 with a lid 113 and an access bore 112 with plug 114.

Referring to FIG. 1, hollow vessel 14 has a handle 98 secured thereto adjacent top 18. Containment and treatment aspirator system 10, hollow vessel 14, base 17, valving 58, and vacuum/pressure source 36 all rest on a pair of wheels 96 and leg 108.

The container and treatment aspirator system 10 of the invention is designed for aspirating potentially hazardous flowable materials from a surface, vessel, or other surroundings where containment and treatment of potentially hazardous flowable materials is necessary. Potentially hazardous flowable materials as used herein shall include, but not be limited by, the following substances: bodily fluids, arterial fluids, flowable industrial wastes that are a threat to the environment, flowable toxins, flowable carcinogens, mixtures thereof, and the like.

In operation, containment and treatment aspirator system 10 is moved into a desired position. Handle 98 allows a generally backward and downward force on handle 98 to tilt leg 108 from a supporting surface displacing the weight of containment and treatment aspirator system 10 onto wheels 96. On wheels 96, containment and treatment aspirator system 10 can be moved to virtually any location where its use is required.

In the embodiment illustrated, trocar 50 may be secured to receiving end 44 of third conduit 42 and the aspirator system 10 is used for aspirating body and/or arterial fluids from a corpse as it applies to the embalming process. Receiving end 44 is also suitable for the attachment of other accessories such as brushes, scrapers or squeegees for example.

Figure 2:
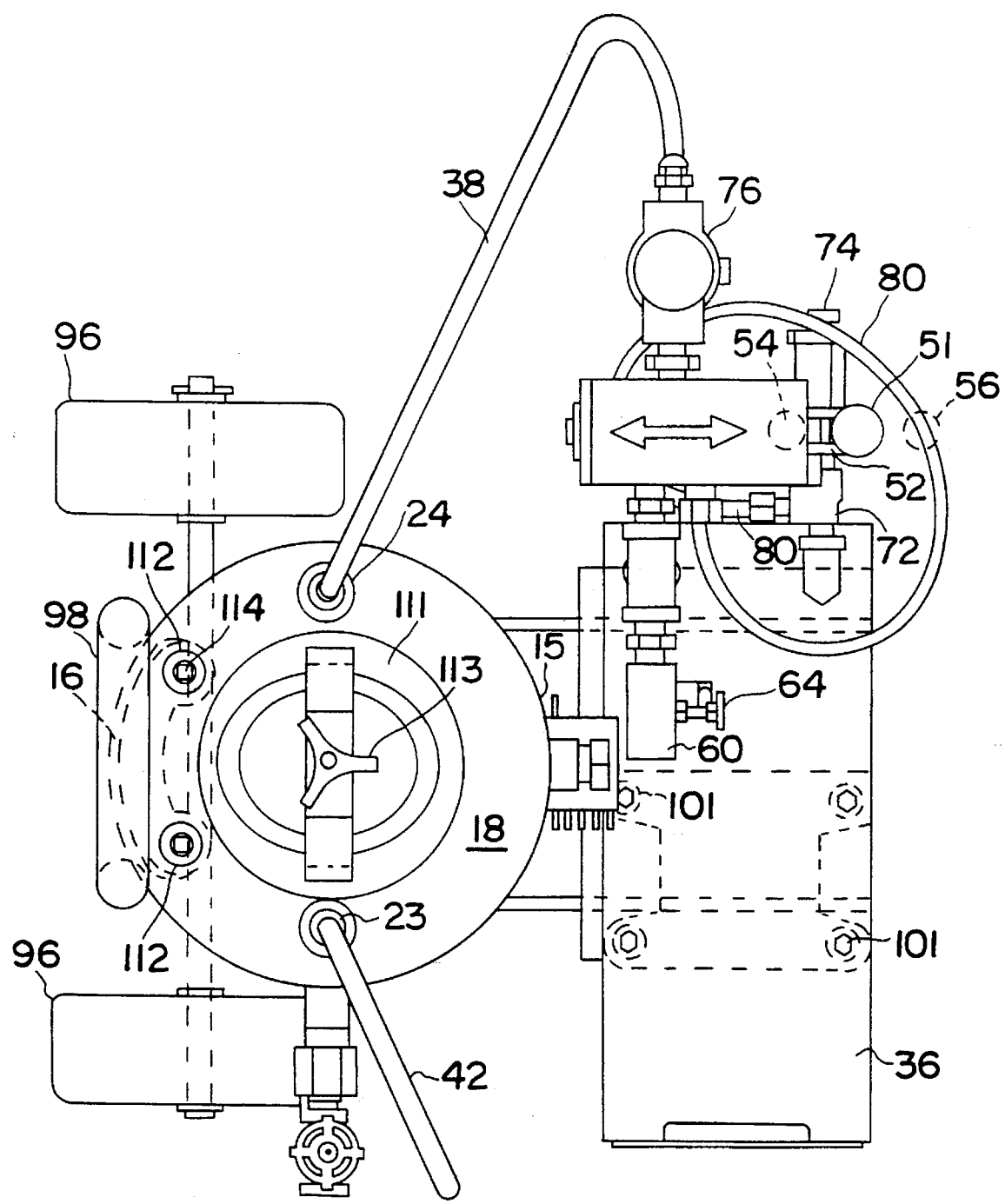
FIG. 2 is a top view of the containment and treatment aspirator system.
Figure 3:
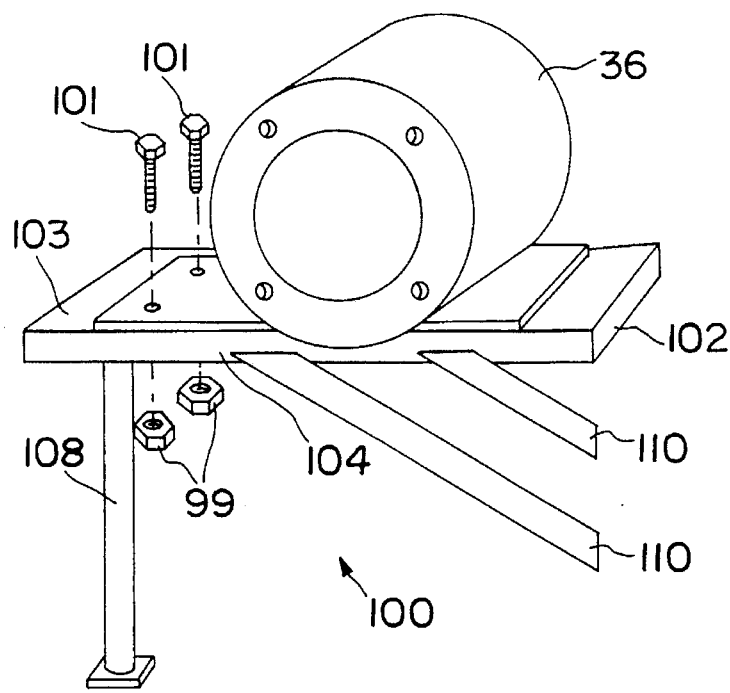
FIG. 3 is a side perspective view of the motor mount of the invention with the motor thereon.

With control valve 52 in its neutral position 51, electric plug 118 is plugged into a normal 115 volt electrical outlet. When receiving end 44 with desired attachment is in place, control valve 52 is moved into vacuum position 54 as illustrated in FIG. 2. This places the containment and treatment aspirator system 10 in its suction mode. Vacuum/pressure source 36 causes air to be evacuated from hollow vessel 14 via liquid trap 76 and second conduit 38 through valving 58. Valving 58 includes vacuum regulator 60, which allows the amount of vacuum to be set and maintained. In a specific embodiment, vacuum regulator 60 allows vacuum to be easily maintained at any value up to 28 inches of mercury.

As air is being removed from hollow vessel 14, valve 48 is opened and suction is caused at receiving end 44 of third conduit 42 and air is aspirated into the exterior of hollow vessel 14 via third conduit 42 and first conduit 26, respectively. As the suction mode continues, flowable material may be drawn into receiving end 44 and deposited in bottom 20 of interior 22. In the specific embodiment used by embalmers, the flowable material may range from liquids to semisolids having consistencies ranging from that which is characteristic of water to flowable wet plaster with suspended solids therein. The suction caused by vacuum/pressure source 36 can be adjusted using vacuum regulator 60.

The flowable material enters vessel 14 adjacent bottom 20. The liquid in vessel 14 soon covers the end of first conduit 26 thereby avoiding splashing and any aspiration of the contents of vessel 14 into outlet port 24. In a specific embodiment, first conduit 26 is placed about 1 inch from bottom 20. Even if flowable liquid is aspirated into port 24, second conduit 38 and liquid trap 76 will remove the same from the aspirated air before the air passes through vacuum/pressure source 36.

Hollow vessel 14 is of suitable volume to hold approximately two or three arterial and body aspirations of corpses. In a specific embodiment, vessel 14 has a volume of about 1,000 fluid ounces. For industrial purposes, the containment and treatment aspirator system 10 can be as large as a truck with a large tank along with adequate valving and plumbing and vacuum source so that tanks of hazardous waste may be transferred and treated accordingly, as well as hazardous fluid spills and other fluid containment and treatment processes.

Valving 58 includes relief valve 64 and emergency relief valve 68. Relief valve 64 can be set to maintain a desired pressure within vessel 14. Emergency relief valve 68 can be used to relieve both vacuum and pressure within vessel 14 depending on the mode of operation without unplugging the aspirator system 10 in the case of an emergency. Additionally, moving control valve 52 into its neutral position 51 will stop vacuum/pressure source 36 and place the system in a neutral mode of not aspirating or pressurizing vessel 14 accordingly.

When the potentially hazardous fluid in vessel 14 reaches a designated level, float 84 connected to external relay 88 causes the vacuum/pressure source 36 to be shut off. This enables the operator to focus on the procedure rather than having to concern himself with the possibility that potentially hazardous fluid reaching top 18 of interior 22 and aspirating into liquid trap 76.

Once vessel 14 of the aspirator system 10 is full, valve 52 is placed in its neutral position 51 and aspirator system 10 is moved as desired to an appropriate drain as desired. Trocar 50 or other implement need not be removed prior to emptying vessel 14. Aspirator system 10 can also be permanently installed over a drain or drain conduit 31 can be permanently plumbed to the sewer.

The discharge mode may be carried out alternatively, with or without utilizing vacuum/pressure source 36 to apply pressure into hollow vessel 14 and more thoroughly discharge the potentially hazardous fluid within interior 22. For one discharge mode, gate valve 32 is placed in its open position and valve 48 is placed in its open position. Flowable material within vessel 14 can then flow through gate valve 32 into the drain or sewer by gravity. Air is vented into vessel 14 through valve 48 during discharge.

Alternatively, control valve 52 is placed in its discharge position 56 and valve 48 is closed. Pressurized air from source 36 is made to flow from source 36 to control valve 52 via fourth conduit 80 through conduit 38 and into vessel 14. The pressure of the air being delivered by source 36 can be adjusted by adjusting pressure regulator 72 accordingly. The pressurized air travels from the source 36 to exit port 24 and into interior 22 via second conduit 38. The pressurized air forces the potentially hazardous flowable materials in interior 22 downwardly and out opening 30 in interior 22 of bottom 20. Potentially hazardous flowable materials exit hollow vessel 14 via drain conduit 31 and gate valve 32 whether liquid, viscous, coagulant, or one of the forgoing flowable materials with or without suspended solids. Gate valve 32, in another embodiment, has plumbing for directing the flow of potentially hazardous flowable materials from gate valve 32 directly to the sewer. This allows for zero amount of contact to be made with the potentially hazardous flowable materials and human beings in the collection, treatment and containment process and provides for essentially odorless operation.

Alternatively, gate valve 32 is placed in its closed position and valve 48 is placed in its open position and control valve 52 is placed in its discharge position 56. The pressurized air from source 36 is made to flow from source 36 to control valve 52 via a fourth conduit 80 through conduit 38 and into vessel 14. The pressure of the air being delivered by source 36 can be adjusted by adjusting pressure regulator 72 accordingly. The pressurized air travels from source 36 to exit port 24 and into interior 22 via second conduit 38. The pressurized air forces the potentially hazardous flowable materials from interior 22 downwardly and outwardly through first conduit 26 and third conduit 42. Potentially hazardous flowable materials exit hollow vessel 14 via third conduit 42 thereby allowing the conduit to be controllably positioned as desired without moving the containment and treatment aspirator system 10.

After the hollow vessel 14 is emptied, gate valve 32 is closed and lid 113 and/or plug 114, as shown in FIG. 2 can be removed and cleaning solution placed in interior 22 of hollow vessel 14. An embodiment has hollow vessel 14 being detachably secured to lower portion 19 of base 17, thus providing for more convenient and accessible cleaning of interior 22 as shown in FIG. 1. The residue left after cleaning and the cleaning solution can be drained from hollow vessel 14 as herein described by positioning gate valve 32 in its open position and allowing the contents to drain, or applying pressure from source 36 as above described. This cleaning procedure can be repeated as required.

The containment and treatment aspirator system 10 of the invention also can be used for treatment of potentially hazardous flowable materials at the time they are collected in interior 22 of hollow vessel 14. Disinfectants, neutralizing agents, germicides, or any like substance rendering potentially hazardous flowable materials harmless can be placed in interior 22 prior to using containment and treatment aspirator system 10 of the invention. This insures the safe treatment without contact with human beings of potentially hazardous flowable materials while in hollow vessel 14. In the case of bodily and arterial fluids, a disinfectant may be used, thus rendering the same harmless to human beings and the environment and able to be discharged down a drain safely. A neutralizing agent, or other substance can be used in industrial applications where potentially hazardous flowable material include strong acidic or basic solutions, thus rendering the same more or less environmentally safe.

Because of the flowable material entering vessel 14 adjacent bottom 20, the flowable material will be ultimately mixed with whatever elements are placed within vessel 14 prior to filling. In a specific embodiment, the distal end of first conduit 26 is covered by the chemicals placed in vessel 14 before suction of the potentially hazardous materials into vessel 14.

After cleaning hollow vessel 14, plug 114 and lid 113 are replaced and secured in an airtight fashion and the container and treatment aspirator system 10 of the invention is ready for reuse. Prior to reuse, however, the liquid trap 76 should be checked and, if necessary, cup 77 must be removed and the contents disposed of accordingly.

If desirable, the contents of cup 77 may be poured into interior 22 of hollow vessel 14 prior to performing the discharge mode as above-described.

The containment and treatment aspirator system 10 of the invention is designed to operate under constant vacuum or constant pressure allowing its operator to focus on the procedure without concern for the fluid pressure in the locality. Treatment liquids may be chosen from the formaldehydes, phenols, alcohols, bleaches, germicides, disinfectants, neutralizers or other such substances and combinations thereof and may be placed in interior 22 before starting the procedure which allows safe draining into the sewer without worry about contamination. Because the vacuum/pressure source 36 is at all times external of the potentially hazardous flowable material, there is no need to use water to aspirate or circulate through the corpse, since the vacuum created by source 36 aspirates body fluid and arterial fluid directly into vessel 14 where it is disinfected and/or neutralized. Body fluids or chemicals do not circulate through source 36 but are pulled into vessel 14 via the third conduit 42.

The containment and treatment aspirator system 10 of the invention is mobile and can be located anywhere in the room or transported to a central drainage place, as desired. One embodiment has hollow vessel 14 made of type 316 stainless steel and an electro polished surface giving the exterior of hollow vessel 14 a mirror like finish.

In a specific embodiment, the containment and treatment aspirator system 10 of the invention can be utilized in accordance with the method of the invention. In performing the method of the invention, distal end 44 of third conduit 42 is outfitted with a trocar 50 which is inserted into a vein of a corpse 125. The veins and arteries of a corpse compose a network which will be aspirated by the aspirator system 10 of the invention.

With control valve 52 in its neutral position 51, electric plug 118 is plugged into a normal 115 volt electrical outlet. Control valve 52 is then moved into vacuum position 54 placing aspirator system 10 in its suction mode. Vacuum/pressure source 36 causes air to be evacuated from hollow vessel 14 via liquid trap 76 and second conduit 38 through valving 58. Valving 58 includes a vacuum regulator 60 which is set at a small vacuum such as 2 inches of mercury.

As air is being removed from hollow vessel 14, valve 48 is opened and suction is caused at receiving end 44 of third conduit 42 and the body fluids within the vein and arterial network of the corpse is aspirated into the interior of hollow vessel 14 via third conduit 42 and first conduit 26, respectively. As the suction mode continues, flowable material is drawn into receiving end 44 and deposited in bottom 20 of vessel 14.

The flowable material enters vessel 14 adjacent bottom 20. The distal end of first conduit 26 is usually beneath the level of the chemicals placed in vessel 14 prior to aspiration to render the potentially hazardous flowable materials being aspirated from the corpse harmless such that they can be later safely drained into the sewer as above described. These chemicals include disinfectants, neutralizing agents, germicides, and in specific embodiments, include formaldehydes, phenols, alcohols, and bleaches.

The flowable material enters vessel 14 adjacent bottom 20 below the liquid level in vessel 14 thereby avoiding splashing and aspiration of the contents within vessel 14 into outlet port 24. Furthermore, the aspirated liquids enter bottom 20 at a significantly different velocity than the standing liquid in vessel 14 so as to be thoroughly mixed with the liquid within vessel 14 thereby being treated and rendered harmless upon entering vessel 14.

As soon as the flow of bodily fluids into vessel 14 ceases, vacuum regulator 60 is adjusted to a higher vacuum and aspiration continues as above described, until flow again ceases. When the flow again ceases, vacuum regulator 60 is again set to a higher vacuum and aspiration continues. This is repeated until no more bodily fluids can be aspirated from the veined and arterial network of the corpse. In a specific embodiment, this occurs where the vacuum is so strong that the veined and arterial network collapses. In specific embodiments, this may occur between 14 and 28 inches of mercury. In a specific embodiment, aspiration is achieved by raising the vacuum by increments of 2 inches of mercury until the veined and arterial network collapses.

Once the flow of bodily fluids from the corpse ceases, the vacuum regulator 60 is decreased in vacuum incrementally as it was raised as above described to insure that the bodily fluids are completely aspirated from the veined and arterial network.

Figure 4:
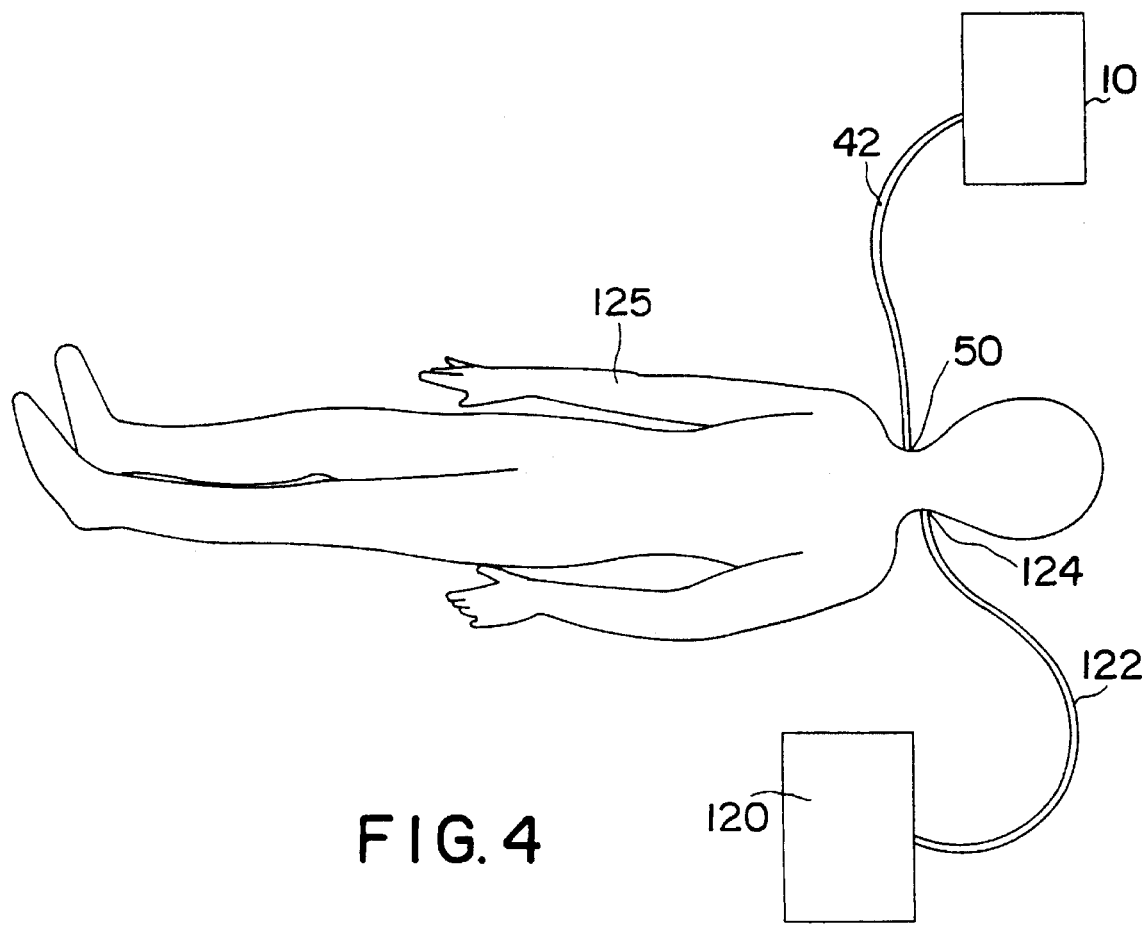
FIG. 4 a diagrammatic view illustrating the method of the invention.

In another specific embodiment of the method of the invention, fluid reservoir 120 is connected by a fluid conduit 122 and a trocar 124 to an artery of the same corpse as shown in FIG. 4. In this embodiment, reservoir 120 is filled with embalming fluid and the method of aspirating a corpse as above described is conducted whereupon embalming fluid is drawn into the veined and arterial network of the corpse as bodily fluids are aspirated therefrom. In performing the aspiration method as above described, the incremental aspiration steps are performed until either no bodily fluids are flowing into vessel 14 or the liquid being aspirated appears to be embalming fluid rather than bodily fluids. Like the aspirating method above described, each incremental step is performed utilizing a vacuum, maintained by vacuum regulator 60, which is raised, incrementally, until the veined and arterial network of the corpse collapses. At this time, the vacuum caused by vacuum/pressure source 36 is incrementally reduced to atmospheric pressure as above described insuring that all of the bodily fluids are aspirated from the veined and arterial network of the corpse.

In a specific embodiment of the aspirator system 10, hollow vessel 14 is of suitable volume to hold bodily fluids from a plurality of corpses. Whenever vessel 14 of aspirator system 10 is full, valve 52 is placed in its neutral position 58, the discharge mode may be carried out alternatively in accordance with any one of the three discharge procedures above described, and the aspirator system 10 can be cleaned periodically as above described.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A reusable apparatus for collection, treatment, containment and safe discharge of potentially hazardous flowable materials comprising a hollow vessel with a top and a bottom, said vessel having an inlet port and an outlet port therein, a first conduit being secured to said inlet port, said first conduit terminating adjacent said bottom, thereby providing a means by which fluids in said vessel can be discharged therefrom when pressure is applied within said vessel through said outlet port, said bottom having a drain opening therein, a vacuum/pressure source exterior of said vessel being connected to said outlet port through valving by a second conduit whereby air can be selectively exhausted from said vessel to said source to provide said vessel with varied degrees of vacuum as desired for collecting fluids therein and whereby said vessel can be selectively pressurized for discharging fluids therefrom, said first conduit having a distal end exterior of vessel whereby flowable liquids can be sucked into said vessel via said first conduit thereby collecting and containing potentially hazardous flowable materials in said hollow vessel and safely discharging said materials from said vessel.

2. The apparatus of claim 1 wherein said distal end bas a trocar secured thereto, whereby arterial and body fluids can be aspirated from a corpse.

3. The apparatus of claim 1 wherein said vacuum pressure source is a pump driven by a motor chosen from the group consisting of electric and internal combustion motors.

4. The apparatus of claim 1 wherein said valving includes a vacuum source control valve with a vacuum position and a discharge position, whereby said vacuum source control valve has a suction mode and a discharge mode.

5. The apparatus of claim 4 wherein said outlet port and said second conduit and said control valve and said vacuum source are plumbed together, said vacuum/pressure source also being a source of pressurized air, whereby air can flow from said vessel to said vacuum/pressure source and from said vacuum/pressure source to said vessel, thereby defining respectively said suction mode and a pressurized discharge mode.

6. The apparatus of claim 1 wherein said drain opening is plumbed through a valve having an open position and a closed position, whereby said flowable materials can be discharged from said hollow vessel.

7. The apparatus of claim 1 further comprising a float within said vessel and a switch mounted external of said vessel between a power source and said vacuum/pressure source, said switch being normally on, said switch being off when said material in said vessel raises said float.

8. The apparatus of claim 1 wherein said valving includes a vacuum regulator, a vacuum relief valve, an emergency relief valve and a pressure regulator whereby said vacuum/ pressure source has variable pressure and suction strengths as desired.

9. The apparatus of claim 8 further comprising a liquid trap positioned between said valving and said vessel.

10. The apparatus of claim 1 wherein said valving has a neutral position in which no air is being exhausted from said vessel and no air is being added to said vessel.

11. The apparatus of claim 1 wherein said vessel has an interior and a cleaning port, said cleaning port having a size through which cleaning utensils can be used to clean said interior of said vessel.

12. The apparatus of claim 1 wherein said vessel is mounted on an axle, said axle having opposite ends, wheels on said axle at said opposite ends, a platform extending from said vessel and generally perpendicularly of said axle, said vacuum/pressure source being mounted on said platform, a leg secured to said platform and extending downwardly therefrom supporting said vessel with said wheels.

13. The apparatus of claim 12 wherein a handle is secured to said vessel, said handle being on one side of said axle, said apparatus having a center of gravity on the side opposite said one side of said axle, said handle providing a mechanical advantage whereby said vessel may be rotated about said axle and totally supported on said wheels for moving said vessel as desired.

14. The apparatus of claim 1 wherein said vacuum/ pressure source is operable to draw flowable liquids into said vessel through said first conduit, said flowable liquids exiting said first conduit and entering said vessel adjacent said bottom of said vessel, said incoming flowable liquid agitating said flowable liquid in said vessel, said incoming flowable liquid essentially not splashing and essentially not exiting with air through said second conduit.

15. A reusable collection, treatment, and safe discharge aspirator system comprising a hollow vessel with a top and a bottom, said top having an inlet and an outlet port therein, a first conduit being secured to said inlet port, said first conduit terminating adjacent said bottom, thereby providing a means by which fluids in said vessel can be discharged therefrom when pressure is applied within said vessel through said outlet port, a treatment liquid vessel portion between said first conduit and said bottom, said bottom having a drain opening therein, a vacuum/pressure source, said vacuum/pressure source being exterior of said vessel and connected to said outlet port by a second conduit, said first conduit having a receiving end, a trocar secured to said receiving end, control valving with a vacuum portion and a pressure position operatively connected to said vacuum/ pressure source, whereby air can be selectively exhausted from said vessel to said vacuum/pressure source causing potentially hazardous flowable material to be sucked into said vessel and mixed with treatment liquid in said vessel and whereby said vessel can be selectively pressurized for discharging fluids through said drain opening under pressure, said flowable materials at all times being separated from said vacuum source.

16. The apparatus of claim 15 wherein said valving includes a vacuum regulator and a vacuum relief valve, whereby said vacuum/pressure can have a variable vacuum strength as desired, and an emergency relief valve, said valving being connected to said vacuum/pressure whereby air can flow from said vessel to said vacuum/pressure, thereby defining a suction mode.

17. The apparatus of claim 15 wherein said control valving and said outlet port have a liquid trap connected therebetween, thereby preventing potentially hazardous flowable material from flowing into said vacuum/pressure when said vacuum/pressure is in a suction mode.

18. The apparatus of claim 15 wherein said vacuum/ pressure has a pressure regulator connected thereto, said pressure regulator and said control valving being connected by a third conduit, whereby air can flow from said vacuum/ pressure to said control valving and to said vessel at a variable and desired pressure, thereby defining a discharge mode.

19. The apparatus of claim 15 wherein said aspirator has a float positioned in said vessel, said float being connected to an external relay, said relay communicating with said vacuum/pressure, whereby when potentially hazardous flowable material in said hollow vessel reaches a designated level, said float actuates said relay terminating operation of said vacuum/pressure.

20. The apparatus of claim 15, wherein said hollow vessel has a front and a back, said hollow vessel being secured to a hollow shell, said hollow shell extending downwardly from said bottom, said hollow shell having a lower portion beneath said bottom, an axle with a pair of wheels secured to said lower portion, a handle secured to said back, whereby said vessel can be tilted by said handle onto said wheels and moved as desired.

21. The apparatus of claim 15 wherein a vacuum/pressure mount is secured to said vessel, said mount having a platform, a leg, and a pair of supports, said supports being secured between said front and said platform, respectively, said platform extending outwardly from said front, said leg being secured to said platform and depending therefrom, said source mount being secured to said platform, whereby said source mount and vessel are movable as a single unit.

22. The apparatus of claim 15 further comprising treatment liquids in said vessel portion, said treatment liquids are chosen from the group consisting of formaldehydes, phenols, alcohols, bleaches, germicides, disinfectants and neutralizers.

23. The apparatus of claim 15 wherein said vessel is made of 316 stainless steel.

24. The apparatus of claim 15 further comprising a valve in said first conduit.

25. A reusable apparatus for collection, treatment, containment and safe discharge of potentially hazardous flowable materials comprising a hollow vessel with a top and a bottom, said top having an inlet port and an outlet port therein, a first conduit being secured to said inlet port, said first conduit extending downwardly from said top within said vessel and terminating adjacent said bottom, thereby providing a means by which fluids in said vessel can be discharged therefrom when pressure is applied within said vessel through said outlet port, said bottom having a drain opening therein, a vacuum/pressure source connected to said outlet port through valving by a second conduit whereby air can be selectively exhausted from said vessel to said vacuum/pressure source for collecting fluids in said vessel and whereby said vessel can be Selectively pressurized for discharging fluids therein, a third conduit with a distal end and a port end, said port end being secured to said inlet port whereby flowable liquids can be sucked into said vessel via said third and first conduits, respectively, when air is exhausted from said vessel to said vacuum/pressure source, a valve in said second conduit, whereby contents of said vessel may be exhausted from said vessel through said first and third conduits and said drain opening when said vessel is pressurized.

* * * * *